United States Patent [19]

Braun et al.

[11] 4,082,460
[45] Apr. 4, 1978

[54] GRAPHITE TUBE FOR USE IN A FLAMELESS ATOMIC ABSORPTION SPECTROMETER

[75] Inventors: Klaus Joachim Braun, Überlingen; Hans Gunter Gerhard Siess, Owingen, both of Germany

[73] Assignee: Bodenseewerk Perkin-Elmer & Co., GmbH, Überlingen (Bodensee), Germany

[21] Appl. No.: 738,478

[22] Filed: Nov. 3, 1976

[30] Foreign Application Priority Data

Dec. 29, 1975  Germany ............................. 2558948

[51] Int. Cl.$^2$ ............................................. G01N 21/54
[52] U.S. Cl. ...................................... 356/85; 356/244
[58] Field of Search ...................... 356/43, 44, 85, 244

[56] References Cited

U.S. PATENT DOCUMENTS

| 3,817,629 | 6/1974 | Witte | 356/244 |
| 3,862,805 | 1/1975 | Tamm et al. | 356/244 |

*Primary Examiner*—John K. Corbin
*Assistant Examiner*—Matthew W. Koren
*Attorney, Agent, or Firm*—S. A. Giarratana; F. L. Masselle; J. D. Crane

[57] ABSTRACT

An improved graphite tube for use in a flameless atomic absorption spectrometer, which is characterized by a mechanically roughened area on at least a portion of the outer peripheral surface of the graphite tube for providing substantially constant emissivity for pyrometric temperature measurement, and in a preferred form the mechanically roughened area has superimposed thereon a microscopic chemically roughened area.

6 Claims, 2 Drawing Figures

GRAPHITE TUBE FOR USE IN A FLAMELESS ATOMIC ABSORPTION SPECTROMETER

BACKGROUND OF THE INVENTION

This invention relates to flameless atomic absorption spectroscopy, and more particularly to a new and improved graphite tube for use in measuring the flameless atomic absorption.

In flameless atomic absorption spectroscopy, the path of the rays of a photometer is directed through the longitudinal bore of a small graphite tube. The sample to be analyzed is introduced into this graphite tube, and the tube is then heated to high temperature by passing an electrical current therethrough. The sample is dried, ashed and eventually atomized so that a cloud of atoms is generated within the graphite tube, and the absorption of the cloud is then measured. During this procedure the graphite tube is maintained within an atmosphere of inert gas.

It will be appreciated that it is desirable to measure the temperature of the graphite tube during the aforesaid procedure. Such a measurement can be effected by pyrometric means, i.e. by measurement of the radiation emitted by the graphite tube. However, this involves the problem that in conventional graphite tubes, the emissivity of the surface and thus the radiation emitted at a certain temperature of the graphite tube is not constant, but varies during the course of use. That is, the emissivity of the graphite tube surface and thus the emission is initially relatively low, but during the course of repeated operations it increases until it finally reaches its final value. As a consequence the pyrometer is not able to give reliable and accurate measurements with any given graphite tube, and the accuracy is still worse for different or replacement tubes.

It is known to measure the temperature of workpieces in inductive heating devices by means of optical pyrometers, wherein the workpieces, prior to their insertion into the heating device, are painted at their measuring areas. This paint is so selected as to retain its characteristics unchanged under the influence of heat, as described in German Specification No. 1 145 383. However, such a paint can not be used at the temperatures required for atomic absorption spectroscopy and, furthermore, the vaporizing components of this paint would disturb the absorption measurement.

SUMMARY OF THE INVENTION

With the foregoing state of the art in view, it is the primary general object of the invention to overcome or at least mitigate the problems and shortcomings outlined above.

A more specific overall object of the invention is to provide a graphite tube for flameless atomic absorption spectroscopy, the surface of which has constant emissivity over a long period of operation, whereby reliable pyrometric temperature measurement can be effected therewith.

To the accomplishment of the foregoing and other objectives, the invention contemplates the provision of a new and improved graphite tube for use in a flameless atomic absorption spectrometer, which is characterized by a mechanically roughened area on at least a portion of the outer peripheral surface of the graphite tube for providing substantially constant emissivity for pyrometric temperature measurement.

According to one aspect of the invention, the mechanically roughened area on at least a portion of the outer peripheral surface of the graphite tube comprises a plurality of closely adjacent circumferential gooves which, perferrably, have cross sections in the form of acute triangles. Further, according to another aspect of the invention, the walls of the grooves, in cross-sectional view, form an angle of about 60°.

As another important aspect of the invention, the mechanically roughened area on at least a portion of the outer surface of the graphite tube has superimposed thereon a microscopic chemically roughened area.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which the disclosure is based may readily be utilized as a basis for the designing of other devices for carrying out the several purposes of the invention. It is important, therefore, that the claims be regarded as including such equivalent devices as do not depart from the spirit and scope of the invention.

A specific embodiment of the invention has been chosen for purposes of illustration and description, and is shown in the accompanying drawings, forming a part of the specification.

DETAILED DESCRIPTION OF THE PREFERRED EMBODIMENT

Figure 1:
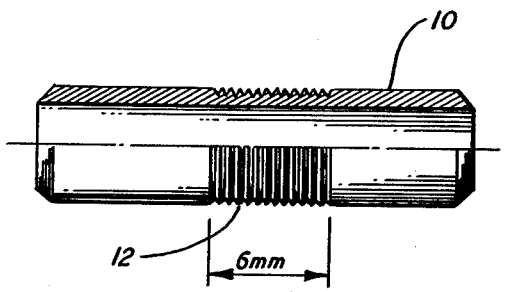
FIG. 1 is a side elevational view, partially in section, of a graphite tube constructed in accordance with the concepts of the invention.

In the embodiment of the invention illustrated in the drawings, a graphite tube 10, for use in an atomic absorption spectometer, has a portion 12 which, for example, is about six millimeters wide, provided with a mechanically roughened area in the form of a plurality of closely adjacent circumferential grooves 14. In a preferred embodiment the circumferential grooves 14 have cross sections in the form of acute triangles, and the walls of the grooves 14, in cross sectional view, form an angle of about 60°. The grooves 14 have a width of about 0.2 millimeters and a depth of about 0.17 millimeters.

It will be appreciated that the mechanical roughened area 12 may be effected by other suitable means such as, for example, by means of sandblasting. However, the use of circumferential grooves 14 is particularly advantageous because they can be machined in an exactly reproducible manner and are not dependent on hard-to-control parameters, such as air pressure and grain size, which may affect the result in sandblasting.

A further improvement lending to constant emissivity is effected by superimposing on the mechanical-macroscopic roughened area 12 a microscopic roughened area produced by chemical means. This can be effected, for example, by heating the graphite tube until it glows in a free atmosphere at about 1000° C centigrade for about 5 seconds. The microscopic roughening can also be produced during the final cleaning of the graphite tube prior to its use by heating the tube until it glows in a chlorine gas flow.

Figure 2:
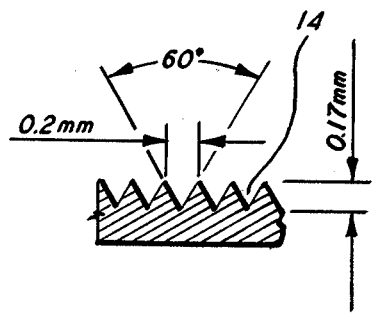
FIG. 2 is an enlarged fragmentary sectional view of a portion of the graphite tube illustrated in FIG. 1.

It has been found that graphite tubes according to the invention, after being heated to a red-hot temperature prior to being put into operation, immediately have a high emissivity rate, which they maintain nearly unchanged until the end of their useful life. In addition, the differences in the emissivity characteristics between one tube and another tube are very small. Moreover, the graphite tubes provided with the grooves, as shown in FIGS. 1 and 2, have the advantage that if they are touched by the hand of an operator the emissivity characteristics are substantially unaffected, as the radiating surfaces are protectively located within the grooves. This is a particular advantage of the circumferential groove arrangement as compared to the sandblasting technique of forming the mechanically roughened area.

Having thus described the invention with particular reference to the preferred forms thereof, it will be obvious to those skilled in the art to which the invention pertains, after understanding the invention that various changes and modifications may be made therein without departing from the spirit and scope of the invention, as defined by the claims appended hereto.

What is claimed is:

1. In an atomic absorption spectrometer for measuring the flameless absorption of samples having a graphite tube for receiving said samples, the improvement comprising a mechanically roughened area on at least a portion of the outer peripheral surface of said graphite tube for providing substantially constant emissivity for pyrometric temperature measurement.

2. The device of claim 1 wherein said roughened area on at least a portion of the outer peripheral surface of the graphite tube comprises a plurality of closely adjacent circumferential grooves.

3. The devices of claim 2 wherein said closely adjacent circumferential grooves have cross sections in the form of acute triangles.

4. The device of claim 3 wherein the walls of said grooves, in a cross-sectional view, form an angle of about 60°.

5. The device of claim 4 wherein said grooves have a width of about 0.2 millimeters and a depth of about 0.17 millimeters.

6. The device of claim 1 wherein said mechanically roughened area on at least a portion of the outer peripheral surface of the graphite tube has superimposed thereon a microscopic chemically roughened area.

* * * * *